US010676719B2

(12) United States Patent
Mao et al.

(10) Patent No.: US 10,676,719 B2
(45) Date of Patent: Jun. 9, 2020

(54) DEVICES AND METHODS FOR SEPARATING PARTICLES

(71) Applicants: University of Georgia Research Foundation, Inc., Athens, GA (US); Augusta University Research Institute, Inc., Augusta, GA (US)

(72) Inventors: Leidong Mao, Athens, GA (US); Carsten Schroeder, Augusta, GA (US); Wujun Zhao, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 63 days.

(21) Appl. No.: 15/223,515

(22) Filed: Jul. 29, 2016

(65) Prior Publication Data

US 2017/0029782 A1 Feb. 2, 2017

Related U.S. Application Data

(60) Provisional application No. 62/199,263, filed on Jul. 31, 2015.

(51) Int. Cl.
*B01L 3/00* (2006.01)
*C12N 5/09* (2010.01)
*C12N 5/095* (2010.01)

(52) U.S. Cl.
CPC ...... *C12N 5/0693* (2013.01); *B01L 3/502761* (2013.01); *B01L 3/502776* (2013.01); *C12N 5/0695* (2013.01); *B01L 2200/0652* (2013.01); *B01L 2300/0816* (2013.01); *B01L 2300/0883* (2013.01); *B01L 2400/043* (2013.01); *B01L 2400/0487* (2013.01)

(58) Field of Classification Search
CPC ......... B01L 3/502776; B01L 3/502761; B01L 2300/0883; B01L 2300/0861; B01L 2200/0652; B01L 2400/043
See application file for complete search history.

(56) References Cited

U.S. PATENT DOCUMENTS

| 4,756,884 | A | 7/1988 | Hillman et al. |
|---|---|---|---|
| 5,957,298 | A | 9/1999 | Buske et al. |
| 6,432,630 | B1 | 8/2002 | Blankenstein |
| 6,482,328 | B1 | 11/2002 | Davidson et al. |
| 6,994,219 | B2 | 2/2006 | Roth et al. |
| 7,186,398 | B2 | 3/2007 | Andres et al. |
| 7,364,921 | B1 | 4/2008 | Sciorra et al. |
| 7,637,941 | B1 * | 12/2009 | Manicka ............ A61L 31/10 623/1.38 |

(Continued)

OTHER PUBLICATIONS

Harouaka, Ramdane A. et al. "Flexible micro spring array device for high-throughput enrichment of viable circulating tumor cells." Clinical Chemistry (2014) 60 323-333. (Year: 2014).*

(Continued)

*Primary Examiner* — Christopher Adam Hixson
(74) *Attorney, Agent, or Firm* — Thomas|Horstemeyer, LLP

(57) ABSTRACT

Devices for non-invasive, label-free separation of particles in liquid, including circulating tumors cells in blood, are provided. Embodiments of the disclosure provide for devices employing magnetic fluids and magnets for separation of circulating tumor cells from blood. Methods for separation of particles including circulating tumor cells are also provided.

17 Claims, 6 Drawing Sheets

(56) References Cited

U.S. PATENT DOCUMENTS

| | | |
|---|---|---|
| 7,658,854 B2 | 2/2010 | Oder et al. |
| 8,083,069 B2 | 12/2011 | Murthy et al. |
| 2003/0159999 A1 | 8/2003 | Oakey et al. |
| 2007/0065808 A1 | 3/2007 | Bohm et al. |
| 2008/0178692 A1 | 7/2008 | Jung et al. |
| 2009/0014360 A1 | 1/2009 | Toner et al. |
| 2009/0050569 A1 | 2/2009 | Jung et al. |
| 2010/0297733 A1 | 11/2010 | Lin et al. |
| 2012/0055854 A1 | 3/2012 | Tibbe |
| 2012/0080360 A1 | 4/2012 | Stone et al. |
| 2013/0306566 A1* | 11/2013 | Mao .................. B03C 1/32 210/695 |

OTHER PUBLICATIONS

Mach, Albert J. et al. "Continuous scalable blood filtration device using inertial nnicrofluidics." Biotechnology and Bioengineering (2010) 107 302-311. (Year: 2010).*

Modak, Nipu et al. "Cell separation in a microfluidic channel using magnetic microspheres." Microfluid. Nanofluid. (2009) 6 647-660. (Year: 2009).*

Muthiah, Muthunarayanan et al. "Surface modification of iron oxide nanoparticles by biocompatible polymers for tissue imaging and targeting." Biotechnology Advances (2013) 31 1224-1236. (Year: 2013).*

Forte, James Andrew, "Nonmagnetic particle separation using ferrofluids controlled by magnetic fields" (2009). Mechanical Engineering Master's Theses. Paper 21. http://hdl.handle.net/2047/d20000033.

Mao, Leidong, "A study of ferrohydrodynamics under traveling magnetic field excitations" (2008). Doctor of Philosophy Dissertation at Yale University. May 2008.

Zhu et al., Continuous separation of non-magnetic particles inside ferrofluids, Apr. 20, 2010, Springer-Verlag, Microfluid nanofluid 9, pp. 1003-1009.

Zhu et al., Continuous-flow ferrohydrodynamic sorting of particles and cells in microfluidic devices, Jun. 1, 2012, Springer-Verlag, Microfluid Nanofluid 13, pp. 645-654.

Kose et al., Ferrofluid mediated nanocytometry, Nov. 11, 2011, Royal Society of Chemistry, Lab Chip 12, pp. 190-196.

C. Aggarwal; at al (2013) "Relationship Among Circulating Tumor Cells, CEA and Overall Survival in Patients with Metastatic Colorectal Cancer" Annals of Oncology 24: pp. 420-428.

S. Mocellin; et al (2006) "The Prognostic Value of Circulating Tumor Cells in Patients with Melanoma: A Systematic ReviewandMeta-Analysis" Clin Cancer Res;12(15) pp. 4605-4613.

S. Braun; et al (2004) "Circulating Tumor Cells in Metastatic Breast Cancer—Toward Individualized Treatment?" N. Engl. J. Med. 351;8 pp. 824-826.

S. Paget (1889) "The Distribution of Secondary Growths in Cancer of the Breast" The Lancet, vol. 1. pp. 99-101.

C. Alix-Pnabieres; et al (2013) "Circulating Tumor Cells: Liquid Biopsy of Cancer" Clinical Chemistry 59:1, pp. 110-118.

K. Pantel; et al (2010) "Circulating Tumour Cells in Cancer Patients: Challenges and Perspectives" Trends in Molecular Medicine 16, pp. 398-406.

M. G. Krebs; et al (2011) "Evaluation and Prognostic Significance of Circulating Tumor Cells in Patients With Non-Small-Cell Lung Cancer" Journal of Clinical Oncology, vol. 29, No. 12 pp. 1556-1563.

S. Nagrath; et al (2007) "Isolation of Rare Circulating Tumour Cells in Cancer Patients by Microchip Technology" Nature. 450(7173): pp. 1235-1239.

M. Cristofanilli; et al (2007) "Circulating Tumors Cells in Metastatic Breast Cancer: Biologic Staging Beyond Tumor Burden" Clinical Breast Cancer, vol. 7, No. 6, pp. 471-479.

M. Cristofanilli; et al (2004) "Circulating Tumor Cells, Disease Progression, and Survival in Metastatic Breast Cancer" N. Engl. J. Med 351;8 pp. 781-791.

D. C. Danila; et al (2007) "CirculatingTumor Cell Number and Prognosis in Progressive Castration-Resistant Prostate Cancer" Clin Cancer Res;13(23) pp. 7053-7058.

S. L. Stott; et al (2010) "Isolation of Circulating Tumor Cells Using a Microvortex-Generating Herringbone-Chip" PNAS, vol. 107, No. 43, pp. 18392-18397.

R. E. Rosensweig (1989) "Ferrohydrodynamics" J . Fluid Mech. (1989), vol. 200, pp. 595-599.

Zhao et al (2016) "Label-Free and Continuous-Flow Ferrohydrodynamic Separation of HeLa Cells and Blood Cells in Biocompatible Ferrofluids." Adv. Fund. Mater. 26(22), pp. 3990-3998.

Y. N. Xia; et al (1998) "Soft Lithography" Annu. Rev. Mater. Sci. 28: pp. 153-184.

R. Massart (1981) "Preparation of Aqueous Magnetic Liquids in Alkaline and Acidic Media" IEEE Transactions on Magnetics, vol. MAG-17, No. 2, pp. 1247-1248.

C. Boyer; et al (2010) "The Design and Utility of Polymer-Stabilized Iron-Oxide Nanoparticles for Nanomedicine Applications" NPG Asia Mater. 2(1) pp. 23-20.

Ishihara; et al (2009) "Bioinspired Interface for Nanobiodevices Based on Phospholipid Polymer Chemistry" J. R. Soc. Interface 6, pp. S279-S291.

Jozefczak; et al (2009) "Effect of Poly (Ethylene Glycol) Coating on the Magnetic and Thermal Properties of 3iocompatible Magnetic Liquids" Journal of Magnetism and Magnetic Materials 321, pp. 1505-1508.

Samanta; et al (2008) "Protein-Passivated Fe3O4 Nanoparticles: Low Toxicity and Rapid Heating for Thermal Therapy" J. Mater. Chem., 18, pp. 1204-1208.

Yuan; et al (2006) "Synthesis of Biocompatible Poly[2-(methacryloyloxy)ethyl phosphorylcholine]-Coated Magnetite Nanoparticles" Langmuir, 22, pp. 10989-10993.

* cited by examiner

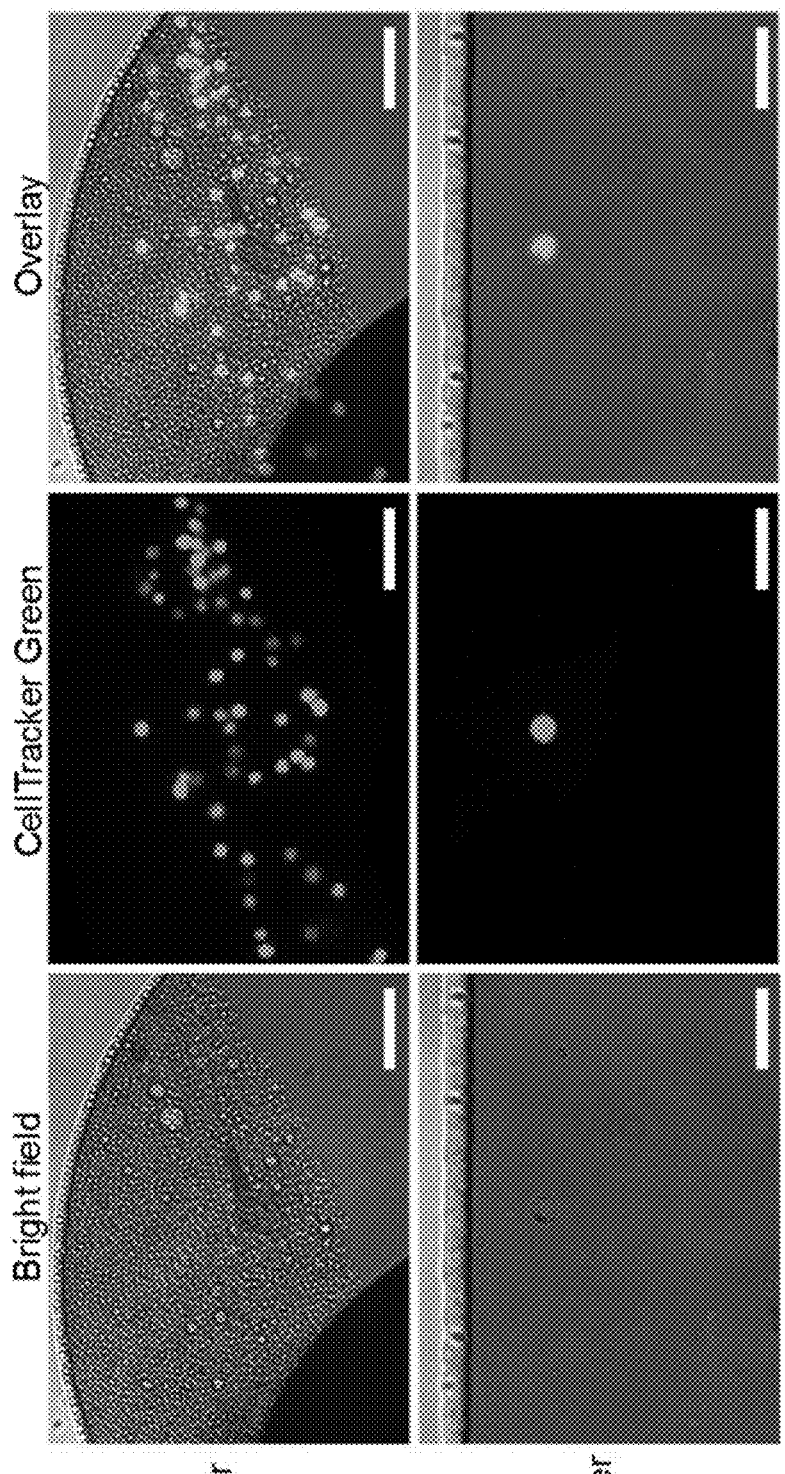

DEVICES AND METHODS FOR SEPARATING PARTICLES

CROSS-REFERENCE TO RELATED APPLICATIONS

This application claims the benefit of and priority to U.S. Provisional Application Ser. No. 62/199,263, having the title "DEVICES AND METHODS FOR SEPARATING PARTICLES," filed on Jul. 31, 2015, the disclosure of which is incorporated herein in by reference in its entirety.

STATEMENT REGARDING FEDERALLY SPONSORED RESEARCH

This invention was made with Government support under Agreement No. GM104528-03, awarded by the National Institutes of Health. The Government has certain rights in the invention.

BACKGROUND

Microfluidic particle and cell sorting plays an important role in environmental monitoring, disease diagnostics, and therapeutics. Some techniques include labeling the particle or cell, however, these techniques have disadvantages. Thus, there is a need to develop alternative techniques for particle sorting.

SUMMARY

Devices for non-invasive, label-free separation of particles in liquid, including circulating tumors cells in blood, are provided. Embodiments of the disclosure provide for devices employing magnetic fluids and magnets for separation of circulating tumor cells from blood. Methods for separation of particles including circulating tumor cells are also provided.

An embodiment of the present disclosure provides for a device, among others, that includes: a serpentine microfluidic channel having a first end and a second end; a first inlet at the first end of the serpentine microfluidic channel, wherein the first inlet is configured to flow a first fluid into the serpentine microfluidic channel, wherein the fluid includes a plurality of components; a filtration region disposed between the first end and the second end, wherein the filtration region includes at least one filter in the serpentine microfluidic channel, wherein the filter removes one or more of the plurality of components; a second inlet located after the first inlet and after the filtration region, wherein the second inlet is configured to combine a second fluid with the first fluid to create a third fluid, and to hydrodynamically focus the components of the third fluid into a stream by sheath flow, wherein the second fluid includes a magnetic fluid; one or more permanent magnets positioned adjacent and along the length of an area of the serpentine microfluidic channel after the second inlet, wherein the permanent magnets are positioned so that the magnetic field produces a magnetization direction perpendicular to the flow of fluid in the serpentine microfluidic channel; and two or more outlet channels positioned after the one or more permanent magnets at the second end. In an embodiment, the first fluid is whole blood and includes unlabeled rare cells. In an embodiment, the serpentine microfluidic channel has at least one curve along the length of the serpentine microfluidic channel, wherein the angle of the curvature is about 120° to about 180°.

An embodiment of the present disclosure includes a method for separating circulating tumor cells from blood cells in a sample of whole blood, among others, that include: introducing the whole blood to a device through the first inlet and flowing the whole blood through the serpentine microfluidic channel, wherein the device is described herein; separating one or more components from the whole blood to form a filtered fluid using at least one filter; introducing the second fluid including the magnetic fluid into the serpentine microfluidic channel through the second inlet to combine with the whole blood to form a third fluid; hydrodynamically focusing the third fluid into a sheath flow; exposing the third fluid to the magnetic field, wherein the magnetic field produces a magnetization direction perpendicular to the flow of filtered fluid in the serpentine microfluidic channel, wherein the components of the filtered fluid are separated as a function of the width of the serpentine microfluidic channel; and collecting portions of the components of the filtered fluid in two or more outlet channels.

Other structures, methods, systems, compositions, features, and advantages will be, or become, apparent to one with skill in the art upon examination of the following drawings and detailed description. It is intended that all such additional structures, systems, methods, features, and advantages be included within this description, be within the scope of the present disclosure, and be protected by the accompanying claims.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

In FIG. 4A, cell mixtures entered and exited the channel together when magnetic fields were not present (top). When the magnetic fields were applied, larger cancer cells were pushed to the Outlet 6 by magnetic buoyancy forces, whereas the smaller WBCs exited through the rest of outlets (bottom). Scale bars: 200 µm. FIG. 4B shows zoomed-in images of 6 outlets when the magnetic fields were present. Scale bars: 100 µm. FIG. 4C is a fluorescence image of cell streaks formed during separation. Lung cancer H1299 cells were stained by CellTracker Green. Red numbers show the outlets. Dashed lines show the microchannel boundaries. Scale bar: 200 µm.

FIG. 6A-B are representative micrographs of lung cancer H1299 cells and WBCs after separation. FIG. 6A shows that lung cancer cells and WBCs were found in the outlet reservoir. Scale bars: 100 µm. FIG. 6B shows that lung cancer cells and WBCs were found in the collection chamber. Scale bars: 50 µm.

DISCUSSION

Figure 1A:
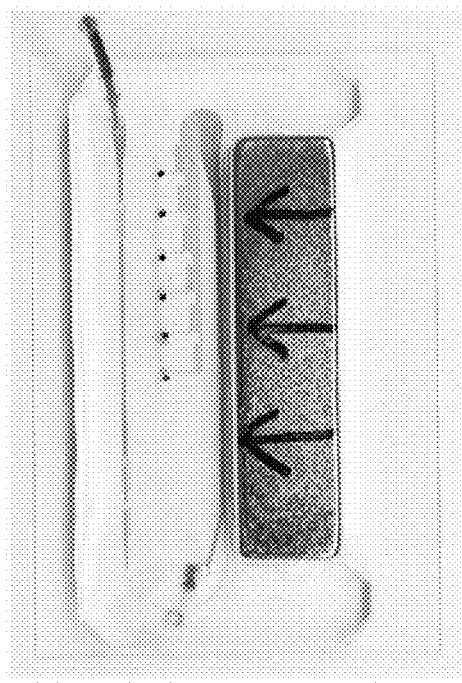
FIG. 1A is a schematic illustration of the separation device with a permanent magnet and a microfluidic channel. Red numbers indicate the outlets.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, material science, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmosphere. Standard temperature and pressure are defined as 25 ° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

A biocompatible substance or fluid, as described herein, indicates that the substance or fluid does not adversely affect the short-term viability or long-term proliferation of a target cell within a particular time range.

Discussion

Embodiments of the present disclosure provide for devices, methods for separating particles, and the like. An embodiment of the present disclosure is advantageous because it has a very high sorting efficiency (e.g., about 95% or more, about 99% or more, about 99.9% or more) and a very high throughput (e.g., about $10^7$ cells/hour or more, about $10^8$ cells/hour or more). In addition, the device is less expensive than other techniques (e.g., FACS) and is straightforward to operate. Embodiments of the present disclosure are advantageous in that neither short-term cell viability nor long-term proliferation of cells are impacted.

In general, embodiments of the present disclosure include non-uniform magnetic field-assisted processes and devices for the separation of particles (e.g., cells) within a magnetic fluid. Under non-uniform magnetic fields, particles such as cells can experience the generated magnetic field direction to produce a magnetic buoyancy force, analogous to buoyancy force, as magnitude of the force is proportional to the volume of cell. This force can be used to spatially separate cells of different sizes in certain flow conditions (e.g., laminar flow and/or shear flow). Embodiments of the present disclosure can be label-free and/or do not require time-consuming steps of magnetic beads conjugation. Although some systems claim to be label-free, embodiments of the present disclosure are truly label-free. Embodiments of the present disclosure include high-efficiency and high-throughput continuous-flow particle separation and focusing devices using magnetic fluid (e.g., ferrofluids) and magnets (e.g., permanent magnets). Permanent magnet based devices are low-cost and easy to operate and their operations does not generate heat. Magnetic fields produced by permanent magnets are substantially larger than the ones by current-carrying electrodes, which can increase the sorting throughput and efficiency of embodiments of the present disclosure.

Embodiments of the present disclosure include a device for separating particles (e.g., components in whole blood). The device includes a serpentine microfluidic channel having a first end and a second end, with a first inlet at the first end of the serpentine microfluidic channel. The first inlet is configured to flow a first fluid into the serpentine microfluidic channel. A second inlet is located after the first inlet and after the filtration region, and the second inlet is configured to combine a second fluid (e.g., a magnetic fluid) with the first fluid to create a third fluid. The components of the third fluid are hydrodynamically focused into a stream by sheath flow. One or more permanent magnets can be positioned adjacent (e.g., 1 or a few mm from the side of the serpentine microfluidic channel) and along the length of an area of the serpentine microfluidic channel after the second inlet, where the permanent magnets are positioned so that the magnetic field produces a magnetization direction perpendicular to the flow of fluid in the serpentine microfluidic channel. The device includes two or more outlet channels positioned after the one or more permanent magnets at the second end. An illustrative embodiment of the device is shown in FIG. 1.

In an embodiment, the first fluid can include a plurality of components, for example whole blood (e.g., white blood cells, red blood cells, circulating tumor cells, and the like). In the device, a filtration region is disposed between the first end and the second end of the device. In an embodiment, the filtration region includes at least one filter in the serpentine microfluidic channel. In an embodiment, the filtration system is disposed prior to the curve immediately before the second inlet and the permanent magnets.

In an exemplary embodiment, the device includes a second inlet in the serpentine microfluidic channel for flowing a second liquid including the magnetic fluid. In an embodiment, additional inlets can be present to introduce other reagents or fluids.

In an embodiment, the whole blood can be flowed in the first inlet and the magnetic fluid can be flowed in a second inlet and the two fluids mix. In an embodiment, the flow rate of the fluid(s) can be controlled and the flow rate can be used to enhance the separation.

In an embodiment the serpentine microfluidic channel can have a constant diameter along its length. In another embodiment, the serpentine microfluidic channel can have a tapered diameter. In an embodiment, the serpentine microfluidic channel can be designed to optimize the separation of the particles.

In an embodiment, the serpentine microfluidic channel can have a length of about 5000 µm to 20000 µm prior to splitting into two or more outlets (e.g., 2 to 100), and a diameter of about 1000 to 2000 µm. In an embodiment, the serpentine microfluidic channel can have a height of about 100 nm to 1000 µm. In an embodiment, the outlets (e.g., outlet channels) can have the same or different diameters and can independently have a diameter of about 500 to 2000 µm. In an embodiment, the outlets can be designed (e.g., diameter, three-dimensional orientation relative to the channel (e.g., offset from the axis of the channel), and the like) to enhance the separation of the particles.

In an embodiment, the serpentine microfluidic channel includes a filtration region after the first inlet and prior to the second inlet. In an embodiment, the filtration region includes one or more filters. In an embodiment, the filter(s) can function to remove large debris or fibrin or irrelevant components in human blood for this particular analysis. In an embodiment, the filter can include a type of filter for blood that can remove large debris or fibrin and the like, and can fit within the dimensions of the serpentine microfluidic channel. In an embodiment, the filter(s) can include a two-row array of 36 S-shaped filters with 18 in each row. In an embodiment, 2 or more filters can be used and the distance between each filter can be about 10 to 40 µm or about 30 µm.

In an embodiment, the serpentine microfluidic channel has at least one curve or turn (e.g., relative to the length and width of the serpentine microfluidic channel) along the length of the serpentine microfluidic channel. In an embodiment, the serpentine microfluidic channel has from 1 to 10 curves or turns. In an embodiment, the curve is after the filtration region. In an embodiment, the angle of the curvature can be about 120° to about 180°.

In an embodiment, the second inlet is positioned after the curve in the serpentine microfluidic channel, and one or more permanent magnets are positioned after the curve.

In an embodiment, the circulating tumor cells are selected from primary cancers including lung cancer, prostate cancer, breast cancer, and pancreatic cancer.

In an exemplary embodiment of the device, a magnetic device configured to direct a non-uniform magnetic force onto particles is positioned at a point of the serpentine microfluidic channel. In an embodiment, the magnetic device can be positioned relative to the split from the serpentine microfluidic channel to the outlets. In an embodiment, the magnetic device is configured to direct the non-uniform magnetic force onto particles from one side of the channel. As noted above, the design of the device (e.g., the position of the magnetic device and/or the outlets) can take into consideration the various components, the particles to be separated, and/or the magnetic fluid, to achieve the desired separation efficiency and/or throughput.

In an embodiment, the magnetic energy can be produced using a magnetic device that includes one or more permanent magnets positioned to produce a non-uniform magnetic field in at least a portion of the serpentine microfluidic channel. In an embodiment, one permanent magnet is disposed on one side of the serpentine microfluidic channel to generate the non-uniform magnetic force. The strength of the magnetic field can be selected based upon the configuration of the device, the particles to be separated (e.g., the volume of the particles), and the like. In another embodiment, the magnetic device includes three or more magnets (e.g., 3, 4, 5, 6, 7, and so on) that can be used to form a non-uniform magnetic field within an area of the channel. The design, number of magnets used, the non-uniform magnetic field generated, and the like, can be designed to separate particles.

As noted above, the device includes a plurality of outlets. Once the non-uniform magnetic force acts upon the particles (e.g., cells in the blood), the particles flow in the first fluid is altered so that certain types of particles flow into one outlet and another type of particle flows into a different outlet.

In an embodiment where many different types of particles are to be separated, then the outlets can be spaced apart along the length of the serpentine microfluidic channel and/or more than one magnet can be used along the length of the serpentine microfluidic channel in conjunction with the spacing of the outlet. Many different types of configurations are envisioned that are consistent with the teachings of the present disclosure and are intended to be covered by claims of this and future application.

In an embodiment, the particles (e.g., blood cells, cancer cells, and the like) can experience non-uniform magnetic force and are biologically compatible with the magnetic fluid. In particular, the particles can be separated by the magnetic buoyancy force exerted upon them. In an embodiment, the particles can include cells, polystyrene microparticles, and a combination thereof. In an embodiment, the cells can include cancer cells, bacterial cells, yeast cells, blood cells, cancer cells, neural cells, sperm cells, eggs, as well as types of cells that have size difference can be distinguished by this technique. In an embodiment, the volume of the cells can be about 5 to 3000 $\mu m^3$.

In an embodiment, the particles are mixed with a magnetic fluid (e.g., prior to introduction to the device and/or within the device). In an embodiment, the magnetic fluid is a colloidal mixture of nano-size magnetic particles (e.g., about 5 to 10 nm in diameter), covered by a surfactant, suspended in a compatible carrier medium. In an embodiment, the magnetic particles can be iron oxide particles, cobalt particles, cobalt ferrite particles, iron particles, and FePt particles, or a combination thereof, where the amount of the magnetic particles in the magnetic fluid can be about 1% (v/v) to 10% (v/v). In an embodiment, the surfactant can include electric double layer surfactant, polymer surfactant, inorganic surfactant, or a combination thereof In an embodiment, the carrier medium can include water, hydrocarbon oil, kerosene, or a combination there. In an embodiment, the magnetic fluid can be a ferrofluid, paramagnetic solution, or a combination thereof.

In an embodiment, the magnetic fluid can include of maghemite nanoparticles ($Fe_2O_3$) coated with polymethyl methacrylate-polyethylene glycol (PMMA-PEG) and 10% (v/v) 10× Hank's balanced salt solution (HBSS). In an embodiment, the volume fraction of maghemite nanoparticles in this ferrofluid can be about 0.2 to 0.3% or about 0.26%.

As mentioned above, embodiments of the present disclosures can include a method for separating circulating tumor cells from blood cells in a sample of whole blood, where the device described herein can be used to perform steps of the method. In an embodiment, the method includes introducing whole blood or a fluid including whole blood to the device through an inlet and flowing the whole blood through a serpentine microfluidic channel. Components from the whole blood are passed through one or more filters to form a filtered fluid. In an embodiment, a magnetic fluid is introduced into the serpentine microfluidic channel through a second inlet to combine with the whole blood forming a third fluid. The third fluid is hydrodynamically focused into a sheath flow. The third fluid is introduced to a magnetic field, where the magnetic field produces a magnetization direction perpendicular to the flow of filtered fluid in the serpentine microfluidic channel. The components of the filtered fluid are separated as a function of the width of the serpentine microfluidic channel, portions of the components of the filtered fluid are collected in two or more outlet channels.

In an embodiment, the fluid is exposed to a non-uniform magnetic force generated by a magnetic device. In an embodiment, the particles experience a magnetic buoyancy force that causes the particles to separate from one another based on the volume of the particles.

As mentioned above, embodiments of the present disclosure include a method for separating components in whole blood, where the device described herein can be used to perform steps of the method. In an embodiment, the method is a continuous flow method. In an embodiment, the first fluid including the whole blood are flowed through the filter. The remaining components are mixed with the magnetic fluid are flowed down the serpentine microfluidic channel having a sheath flow. At a position in the serpentine microfluidic channel (e.g., a first area), the fluid including the components is exposed to a non-uniform magnetic force, where a magnetic device can be used to generate the non-uniform magnetic force. In an embodiment, the components experience a magnetic buoyancy force that causes the components to separate from one another based on the volume of the components. In an embodiment, the components can be separated from one another into two or more outlets.

In an embodiment, this process can be repeated for the components that are separated to increase efficiency and/or separate components having similar characteristics (e.g., volume). For example, the separated flow can be recirculated through the same serpentine microfluidic channel or can be flowed through a different channel. The device may include two or more channels and magnets.

EXAMPLES

Now having described the embodiments of the disclosure, in general, the example describes some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Introduction

Circulating tumor cells (CTCs), which are cells that cast from primary tumors and disseminated through the blood to other organs, enable frequent and minimally invasive access to tumor samples and promise a new approach in monitoring cancer treatment.[1] CTCs are essential in oncology as they serve as a liquid biopsy target in cancer diagnosis and prognosis, as well as in assessing the efficacy of treatment.[2,3] Lung cancer, especially non-small cell lung cancer (NSCLC), is the leading cause of cancer deaths in the United States. Currently, NSCLC patients must undergo bronchoscopy or computed tomography (CT)-guided biopsy for tissue diagnosis or to understand the mechanism of treatment resistance. However, these methods are invasive, expensive, uncomfortable, and have risks of bleeding, pneumothorax, and radiation, and therefore cannot be used frequently. The use of CTCs as a liquid biopsy would permit repeated and painless sampling of tumor cells for the same molecular assays performed on traditional biopsies.[4-6] Moreover, changes in the number of CTCs in the blood, as well as in their genome, after initiation of treatment can help identify whether the tumor, including NSCLC,[7,8] is responding to the treatment[9-11] so that the mechanism of drug resistance might be deciphered. Together, this evidence suggests that capturing CTCs will be an attractive first step to understand the prognostic and predictive markers of responder versus non-responder. This concept provides a radical departure from current approaches. The precise counting of CTCs in the blood circulation may constitute a very powerful tool to monitor treatment efficacy of NSCLC, but it also requires the development of highly sensitive, high-throughput, and low-cost separation technology. However, CTCs are extremely rare in the blood circulation, occurring at a concentration of 1-100 CTCs per milliliter of blood.[5] These cells are dispersed in a background of billions of red blood cells (RBCs) and millions of WBCs, making the separation of CTCs a significant challenge. Most of the existing methods for CTC capture are either expensive, tedious, and requiring multiple additional labels to identify the CTCs or having low throughput and low purity.[8,12] Therefor, there is a critical need to develop label-free, high-throughput, high-efficiency, and low-cost technologies for CTC separation that will keep CTCs alive for further molecular analysis.

Here, we introduce a microfluidic CTC separation technology, which uses biocompatible ferrofluid hydrodynamics (ferrohydrodynamics)[13] to separate the CTCs (lung, prostate and breast cancer cells) from other blood cells, addresses the limitations of other separation techniques with its low cost of production, ease of use, high throughput and high efficiency. Ferrofluids are stable magnetic nanoparticles suspensions used as media in microfluidics for CTC separation.[13] The ferrofluid we developed here is biocompatible that can sustain the viability of target cells for up to several hours with excellent colloidal stability and tunable concentration to allow for cell observation without fluorescent labels.[14] The separation device consists of a microchannel and a permanent magnet. The working mechanism of the device is shown in FIG. 1A. Cell mixtures and ferrofluids are introduced into the channel by a pressure-driven flow. When the magnet is not present near the channel, both CTCs and blood cells enter and exit the channel together, resulting in no separation. When the magnet is placed close to the channel, deflections of cells from their laminar flow paths occur because of the magnetic buoyancy force. The force acting on cells inside ferrofluids is a body force and proportional to the volume of cells, which leads to a spatial separation of cells of different sizes at the end of microchannel. As a result, larger CTCs and smaller blood cells exit through different outlets.

Experimental

Figure 1B:
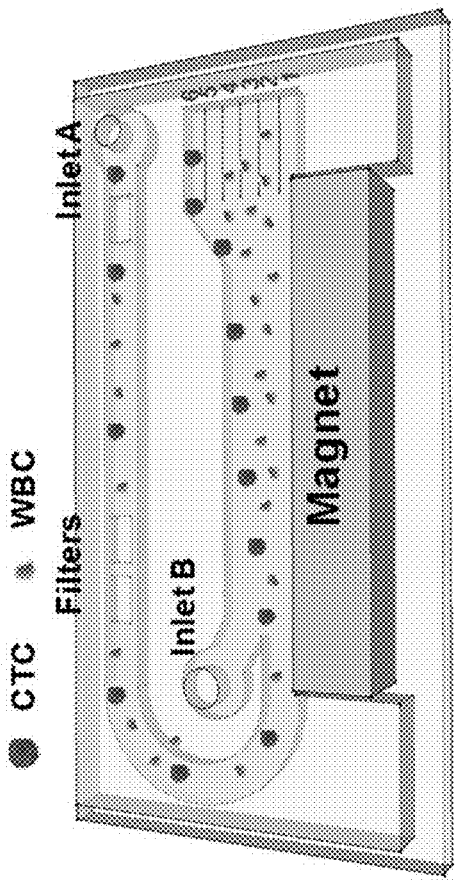
FIG. 1B is an image of the microfluidic device. Magnet was embedded into the PDMS. Black arrows indicate direction of magnet's magnetization. The size of glass slide is 75×50 mm.
Figures 2A, 2B, 2C, 2D:
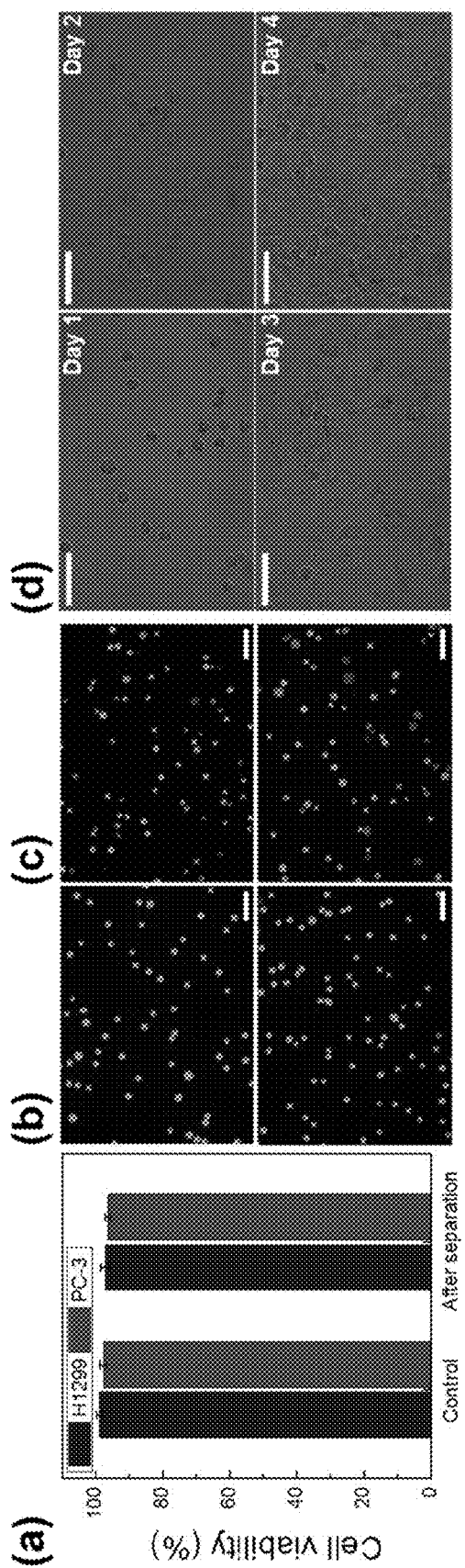
FIG. 2A is a cell viability comparison between control group and after separation group using Live/Dead assays.
FIGS. 2B and 2C are representative fluorescence images of Live/Dead assays for the H1299 2B and PC-3 2C cells. Control group (top) and after separation group (bottom). Calcein-AM (green) and Ethidium homodimer-1 (red) channels were merged. Scale bars: 100 µm. 2D Long-term culture of H1299 cells after separation. Scale bars: 100 µm.

The microfluidic device was fabricated through a standard soft-lithography approach with polydimethylsiloxane (PDMS) layer bonded with a cover glass.[15] A removable NdFeB permanent magnet was placed next to PDMS, which was 1 mm away from the channel with the magnetization direction perpendicular to the channel (FIG. 1B). Ferrofluids were synthesized by chemical co-precipitation method then coated with polymethyl methacrylate-polyethylene glycol (PMMA-PEG).[14,16] Cancer cells (H1299, A549, H3122, PC-3, and MDA-MB-231) were cultured by standard methods. WBCs were prepared by directly lysing of 1 mL of human whole blood and resuspended into 1 mL ferrofluids. CTCs were simulated by spiking 50-2000 CellTracker Green stained cancer cells into 1 mL of WBCs and introduced into Inlet A (FIG. 1A) at a constant flow rate of 100 μL/min, and hydrodynamically focused by a sheath flow from Inlet B at a flow rate of ~120 μL/min. The separated samples were collected into a serpentine collection channel, which was used to accurately enumerate CTCs for the spiked samples after separation.

Results and Discussion

To study the impact of separation platform on cell viability, we first examined both short-term and long-term proliferation after separation. FIGS. 2A-D show that no significant difference was found between control group and after separation group for the short-term viability. Cells were able to spread and grow to confluence after separation. We thus conclude that this separation platform does not have a significant impact on short-term cell viability or long-term proliferation of cells.

Figure 3:
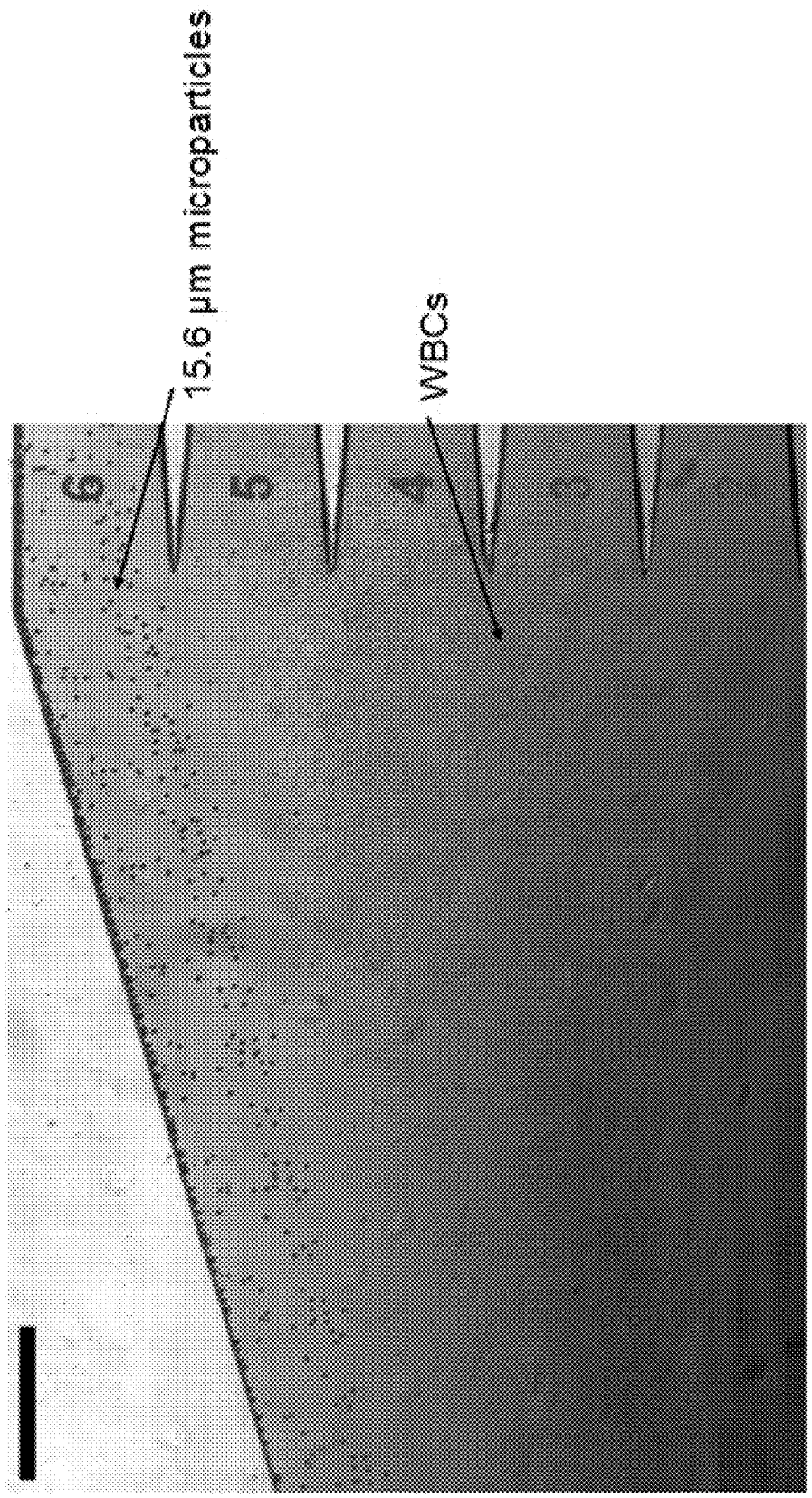
FIG. 3 shows device calibration with 15.6 µm polystyrene microparticles and white blood cells (WBCs). The stacked image was from 30 consecutive frames, 14 frames/s. Outlets are labeled as red numbers. Scale bar: 500 µm.
Figures 4A, 4B, 4C:
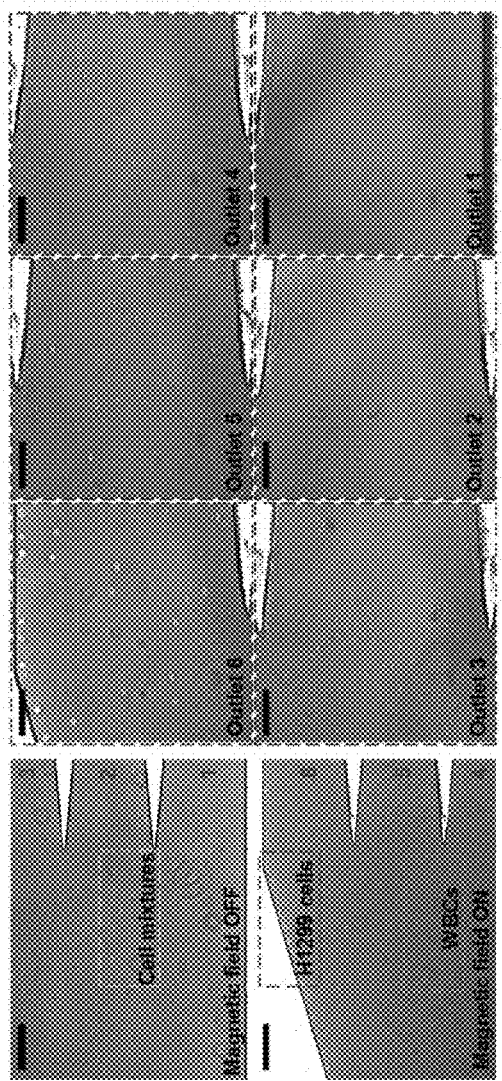
FIGS. 4A-C characterize the performance of microfluidic device via a large number of lung cancer cells H1299 ($1\times10^5$ cells/mL) that were spiked into 1 mL of WBCs.
Figure 5B:
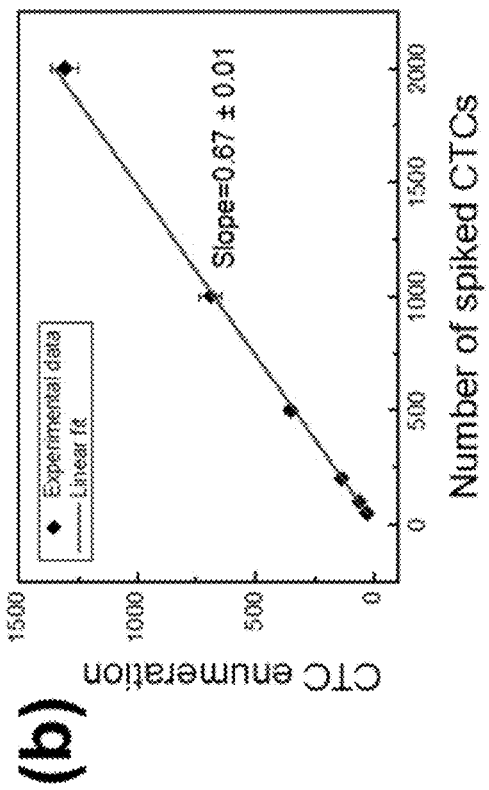
FIG. 5B are results of a series of spike-in separation experiments in which certain number of H1299 cells were spiked into 1 ml of blood to simulate physiological relevant CTC concentration at a flow rate of 100 µL/min. The average separation efficiency was 67%.
Figure 5D:
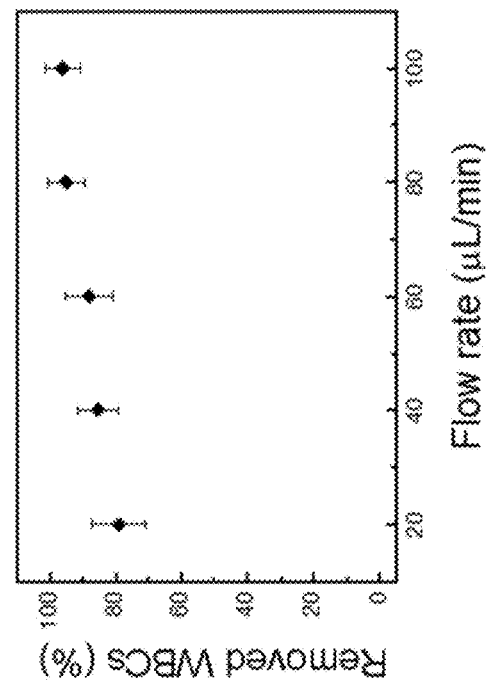
FIG. 5D plots the removal rate of WBCs at different flow rates. About 96% WBCs were removed from the spiked samples at the flow rate of 100 µL/min. Error bars indicate s.d., n=3.
Figure 5A:
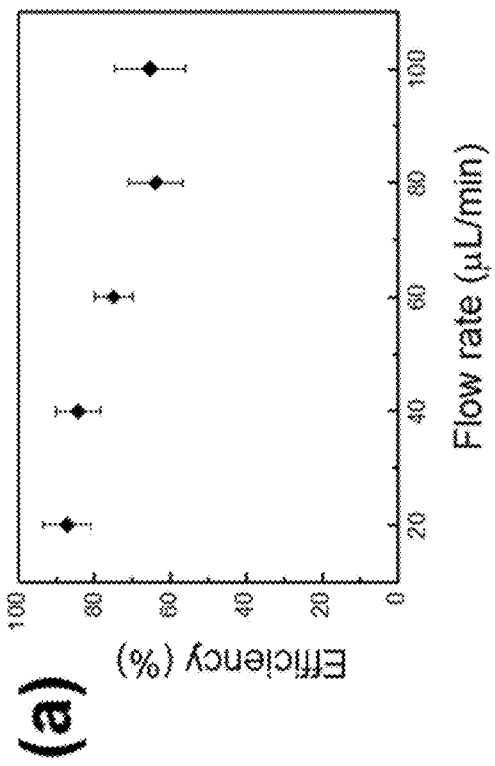
FIG. 5A illustrates separation efficiency of CTCs at different flow rates, the average separation efficiency was 87% and 65% at the flow rate of 20 and 100 µL/min, respectively. 100 H1299 cells were spiked into 1 mL of blood.
Figure 5C:
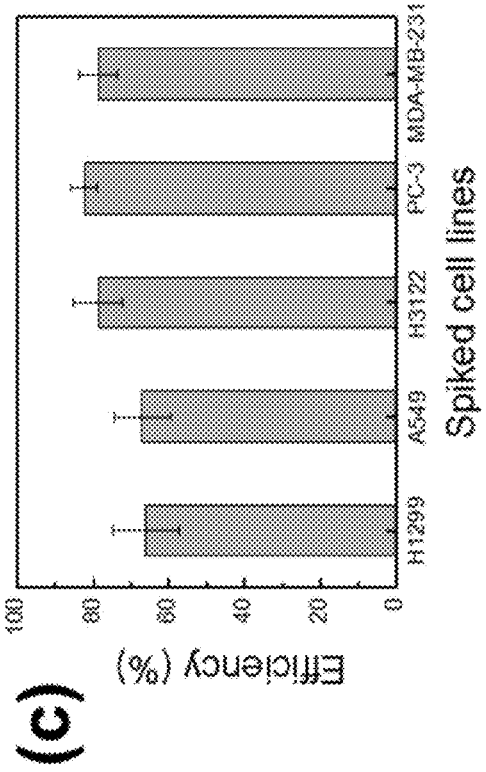
FIG. 5C illustrates the separation efficiency of CTCs with multiple cell lines including H1299 (65%), A549 (67%), H3122 (79%), PC-3(82%), and MDA-MB-231 (79%). 100 CTCs were spiked into 1 mL of blood.

In order to optimize the flow rates for cell separation, we first calibrated the device using polystyrene microparticles with diameter of 15.8 μm (FIG. 3). Recovery rate is defined as the ratio of number of CTCs obtained in Outlet 6 to the number of total CTCs spiked into the blood. FIGS. 4A-C show the micrographs of the separation process with magnetic fields on and off When the magnetic fields were applied, larger CTCs were pushed to the Outlet 6, whereas the smaller WBCs still remained in Outlets 1-5. FIGS. 5A-D summarize the separation efficiency and removal rate of WBCs at different flow rates. The separation efficiency was 65% and the WBC removal rate was 96% at the flow rate of 100 μL/min for the H1299 cells (FIGS. 5A and 5D). In order to simulate physiological relevant CTC concentration in patient blood, we carried out a series of spike-in (50-2000 CTCs/mL) separation experiments. The average separation efficiency was 67%, which is consistent with the previous results (FIG. 5B). FIG. 5C shows the separation efficiency of multiple cell lines, including lung, prostate, and breast cancer cell lines. We achieved the separation efficiency up to 86% for the PC-3 cells. The cell counting results of lung cancer cell lines are summarized in Table 1 and representative images of cell counting form outlet reservoir and collection chamber are shown in FIGS. 6A-B.

TABLE 1

Cell separation with multiple-spiked lung cancer cell lines. 100 CTCs were spiked into 1 mL of blood. The flow rate was 100 μL/min. Cells were collected from each outlet and enumerated under the fluorescence microscopy.

| Cell line | No. of cells spiked | No. of cells collected (Outlet 6) | No. of cells collected (Outlet 5) | No. of cells collected (Outlet 4) | No. of cells collected (Outlet 3) | No. of cells collected (Outlet 2) | No. of cells collected (Outlet 1) | Capture efficiency |
|---|---|---|---|---|---|---|---|---|
| H1299 | ~100 | 76 | 16 | 6 | 0 | 0 | 0 | 76% |
| H1299 | ~100 | 60 | 28 | 18 | 1 | 0 | 0 | 60% |
| H1299 | ~100 | 62 | 20 | 14 | 2 | 0 | 0 | 62% |
| A549 | ~100 | 75 | 18 | 3 | 0 | 0 | 0 | 75% |
| A549 | ~100 | 66 | 22 | 13 | 0 | 0 | 0 | 66% |
| A549 | ~100 | 60 | 21 | 11 | 3 | 0 | 0 | 60% |
| H3122 | ~100 | 72 | 20 | 12 | 0 | 0 | 0 | 72% |
| H3122 | ~100 | 85 | 13 | 4 | 0 | 0 | 0 | 85% |
| H3122 | ~100 | 79 | 8 | 10 | 0 | 0 | 0 | 79% |

Conclusion

We have developed a biocompatible ferrofluid that can sustain the target cells for up to several hours with excellent colloidal stability and tunable concentration to allow for cell observation without labels. We apply this ferrofluid in the continuous-flow separation of CTCs and human blood cells, rendering high throughput and moderate separation efficiency. The developed microfluidic device is capable of processing 6 mL blood per hour with the separation efficiency of 60%-86%. Our method provides significant potential to monitor the phenotypic and genotypic changes in CTCs of cancer patients due to its label-free feature.

References for Example 1

1. C. Aggarwal, N. J. Meropol, C. J. Punt, N. Iannotti, B. H. Saidman, K. D. Sabbath, N. Y. Gabrail, J. Picus, M. A. Morse, E. Mitchell, M. C. Miller and S. J. Cohen, Ann Oncol, 2013, 24, 420-428.
2. S. Mocellin, D. Hoon, A. Ambrosi, D. Nitti and C. R. Rossi, Clin Cancer Res, 2006, 12, 4605-4613.
3. S. Braun and C. Marth, New Engl J Med, 2004, 351, 824-826.
4. S. Paget, Cancer metastasis reviews, 1989, 8, 98-101.
5. C. Alix-Panabieres and K. Pantel, Clinical chemistry, 2013, 59, 110-118.
6. K. Pantel and C. Alix-Panabieres, Trends Mol Med, 2010, 16, 398-406.
7. M. G. Krebs, R. Sloane, L. Priest, L. Lancashire, J. M. Hou, A. Greystoke, T. H. Ward, R. Ferraldeschi, A. Hughes, G. Clack, M. Ranson, C. Dive and F. H. Blackhall, J Clin Oncol, 2011, 29, 1556-1563.
8. S. Nagrath, L. V. Sequist, S. Maheswaran, D. W. Bell, D. Irimia, L. Ulkus, M. R. Smith, E. L. Kwak, S. Digumarthy, A. Muzikansky, P. Ryan, U. J. Balis, R. G. Tompkins, D. A. Haber and M. Toner, Nature, 2007, 450, 1235-U1210.
9. M. Cristofanilli, K. R. Broglio, V. Guarneri, S. Jackson, H. A. Fritsehe, R. Islam, S. Dawood, J. M. Reuben, S. W. Kau, J. M. Lara, S. Krishnamurthy, N. T. Ueno, G. N. Hortobagyi and V. Valero, Clin Breast Cancer, 2007, 7, 471-479.
10. M. Cristofanilli, G. T. Budd, M. J. Ellis, A. Stopeck, J. Matera, M. C. Miller, J. M. Reuben, G. V. Doyle, W. J. Allard, L. W. M. M. Terstappen and D. F. Hayes, New Engl J Med, 2004, 351, 781-791.
11. D. C. Danila, G. Heller, G. A. Gignac, R. Gonzalez-Espinoza, A. Anand, E. Tanaka, H. Lilja, L. Schwartz, S. Larson, M. Fleisher and H. I. Scher, Clin Cancer Res, 2007, 13, 7053-7058.
12. S. L. Stott, C. H. Hsu, D. I. Tsukrov, M. Yu, D. T. Miyamoto, B. A. Waltman, S. M. Rothenberg, A. M. Shah, M. E. Smas, G. K. Korir, F. P. Floyd, A. J. Gilman, J. B. Lord, D. Winokur, S. Springer, D. Irimia, S. Nagrath, L. V. Sequist, R. J. Lee, K. J. Isselbacher, S. Maheswaran, D. A. Haber and M. Toner, Proceedings of the National Academy of Sciences of the United States of America, 2010, 107, 18392-18397.
13. R. E. Rosensweig, Ferrohydrodynamics, Cambridge University Press, Cambridge, 1985.
14. W. Zhao, T. Zhu, R. Cheng, Y. Liu, J. He, H. Qiu, L. Wang, T. Nagy, T. D. Querec, E. R. Unger and L. Mao, Adv Funct Mater, 2016, 26, 3990-3998.
15. Y. N. Xia and G. M. Whitesides, Annu Rev Mater Sci, 1998, 28, 153-184.
16. R. Massart, Ieee T Magn, 1981, 17, 1247-1248.

Example 2

Currently, we are developing a type of water based ferrofluids that can facilitate cervical cancer cells sorting. To maintain the nonmagnetic properties of cancer cells, cellular uptake of magnetic nanoparticles should be minimized. Interaction between cells and magnetic nanoparticles were known to be caused by endocytosis and physical attraction (Verma and Stellacci 2010), which are dictated by the surface properties. Polyethylene glycol and phosphorylcholine based copolymer was chosen as the surfactant to stabilize magnetite ($Fe_3O_4$) nanoparticles for their excellent biocompatibility (Yuan, Armes et al. 2006; Józefczak, Hornowski et al. 2009). Biomimetic phospholipid polar groups were also proven to inhibit non-selective cellular uptake of nanoparticles (Ishihara and Takai 2009). Copolymer structure provides more flexibility with anchoring group and functional group; however, multiple groups can also easily interact with several nanoparticles leading to flocculation (Boyer, Whittaker et al. 2010). Once the colloidal stable ferrofluids are developed, cancer cells viability and cellular uptake of nanoparticles will be measured (Samanta, Yan et al. 2008). Positive results will enable the application of ferrofluids combing microfluidic platform as the cancer cells sorter.

References for Example 2

Boyer, C., M. R. Whittaker, et al. (2010). "The design and utility of polymer-stabilized iron-oxide nanoparticles for nanomedicine applications." *NPG Asia Mater* 2: 23-30.

Ishihara, K. and M. Takai (2009). "Bioinspired interface for nanobiodevices based on phospholipid polymer chemistry." *Journal of The Royal Society Interface* 6 (Suppl 3): S279-S291.

Józefczak, A., T. Hornowski, et al. (2009). "Effect of poly (ethylene glycol) coating on the magnetic and thermal properties of biocompatible magnetic liquids." *Journal of Magnetism and Magnetic Materials* 321(10): 1505-1508.

Samanta, B., H. Yan, et al. (2008). "Protein-passivated Fe304 nanoparticles: low toxicity and rapid heating for thermal therapy." *Journal of Materials Chemistry* 18(11): 1204-1208. Verma, A. and F. Stellacci (2010). "Effect of Surface Properties on Nanoparticle—Cell Interactions." *Small* 6(1): 12-21.

Yuan, J. J., S. P. Armes, et al. (2006). "Synthesis of Biocompatible Poly[2-(methacryloyloxy)ethyl phosphorylcholine]—Coated Magnetite Nanoparticles." *Langmuir* 22(26): 10989-10993.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to the measurement technique and the type of numerical value. In addition, the phrase "about 'x' to 'y'" includes "about 'x' to about 'y'".

Many variations and modifications may be made to the above-described embodiments. All such modifications and

We claim at least the following:

1. A kit for separating unlabeled rare cells from a sample of whole blood, the kit comprising:
    a biocompatible magnetic fluid comprising a plurality of un-conjugated, nano-sized magnetic particles having an average diameter of about 5-10 nm, wherein the nano-sized magnetic particles are covered by a surfactant and suspended in a compatible carrier medium and wherein the volume fraction of nano-sized magnetic particles is about 0.2% to about 1%; and
    a device comprising:
        a serpentine microfluidic channel having a first end and a second end,
        a first inlet at the first end of the serpentine microfluidic channel, wherein the first inlet is configured to flow the sample of whole blood into the serpentine microfluidic channel,
        a filtration region disposed between the first end and the second end and after the first inlet, wherein the filtration region includes at least one filter in the serpentine microfluidic channel, wherein the filter removes one or both of fibrin and large debris from the sample of whole blood,
        a curve along a length of the serpentine microfluidic channel located after the first inlet and the filtration region, wherein the angle of curvature of the curve is about 120° to about 180°,
        a second inlet located after the first inlet, the filtration region, and the curve, wherein the second inlet is configured to flow the biocompatible magnetic fluid into the serpentine microfluidic channel, to combine the magnetic fluid with the sample of whole blood, and to hydrodynamically focus the unlabeled rare cells into a stream by sheath flow,
        one or more permanent magnets positioned adjacent and along a length of the serpentine microfluidic channel after the second inlet, wherein the permanent magnets are positioned to form a non-uniform magnetic field that produces a magnetization direction perpendicular to the flow of the stream containing the unlabeled rare cells such that the unlabeled rare cells and other components of the sample of whole blood experience a magnetic buoyancy force that causes the unlabeled rare cells and other components to spatially separate from one another in the microfluidic channel based on particle volume, and
        two or more outlet channels positioned after the one or more permanent magnets at the second end of the microfluidic channel, wherein the unlabeled rare cells are separated from the sample of whole blood and into one of the two or more outlets with an average separation efficiency of greater than 65% when operated at a flow rate of about 20 µ/min to about 100 µ/min; and
    wherein the unlabeled rare cells are still alive when they are separated from the sample of whole blood.

2. The device of claim 1, wherein the average separation efficiency is greater than 95%.

3. The kit of claim 2, wherein the unlabeled rare cells comprise circulating tumor cells.

4. The kit of claim 3, wherein the circulating tumor cells are selected from the group consisting of primary cancer cells, lung cancer cells, prostate cancer cells, breast cancer cells, pancreatic cancer cells, and a combination thereof.

5. The kit of claim 1, wherein the serpentine microfluidic channel has a diameter of about 1000 µm to about 2000 µm, and wherein the serpentine microfluidic channel has a length of about 5000 µm to about 20000 µm.

6. The kit of claim 3, and wherein the serpentine microfluidic channel is tapered.

7. The kit of claim 1, wherein the outlet channels have the same or different diameters and independently each have a diameter at an opening of about 500 to about 2000 µm.

8. The kit of claim 1, wherein the permanent magnet is configured adjacent the serpentine microfluidic channel to alter the flow of components of the whole blood that have different volumetric sizes.

9. The kit of claim 1, further comprising one or more collection chambers, an observation window, or a combination thereof.

10. A method for separating unlabeled rare cells from a sample of whole blood using a kit according to claim 1, the method comprising:
    introducing the sample of whole blood through the first inlet and flowing the sample of whole blood through the serpentine microfluidic channel at a flow rate of about 20 µL/min to about 100 µL/min,
    separating one or both of fibrin and large debris from the sample of whole blood using the at least one filter in the filtration region,
    introducing the biocompatible magnetic fluid into the serpentine microfluidic channel through the second inlet to combine with the sample of whole blood,
    hydrodynamically focusing the unlabeled rare cells into a stream by sheath flow, and exposing the stream to the non-uniform magnetic field, such that the non-uniform magnetic field produces a magnetization direction perpendicular to the flow of the stream, the unlabeled rare cells are separated from the sample of whole blood and into one of the two or more outlets with an average separation efficiency of about 65% to about 87%, and the unlabeled rare cells are still alive when they are separated from the sample of whole blood.

11. The method of claim 10, wherein the unlabeled rare cells comprise circulating tumor cells.

12. The method of claim 11, wherein the circulating tumor cells are selected from the group consisting of primary cancer cells, lung cancer cells, prostate cancer cells, breast cancer cells, pancreatic cancer cells, and a combination thereof.

13. The kit of claim 1, wherein the nano-sized magnetic particles are iron oxide particles.

14. The kit of claim 1, wherein the surfactant is selected from the group consisting of an electric double layer surfactant, a polymer surfactant, an inorganic surfactant, and a combination thereof.

15. The kit of claim 1, wherein the nano-sized magnetic particles covered by a surfactant comprises maghemite nanoparticles ($Fe_2O_3$) coated with polymethyl methacrylate-polyethylene glycol (PMMA-PEG).

16. The kit of claim 1, wherein the serpentine microfluidic channel has a diameter of about 1000 µm to about 2000 µm and a length of about 5000 µm to about 20000 µm; and
    wherein the two or more outlet channels each have a diameter and each of the diameters is from about 500 µm to about 2000 µm.

17. The kit of claim 15, wherein the volume fraction of maghemite nanoparticles in the biocompatible magnetic fluid is about 0.2 to about 0.3%.

* * * * *